US006365624B1

(12) United States Patent
Davidson et al.

(10) Patent No.: US 6,365,624 B1
(45) Date of Patent: *Apr. 2, 2002

(54) METHOD AND COMPOSITION FOR DELIVERING ZINC TO THE NASAL MEMBRANE

(75) Inventors: Robert S. Davidson, Woodland Hills; Charles Hensley, Redondo Beach, both of CA (US); Gary S. Kehoe, Glendale, AZ (US)

(73) Assignee: Gel Tech, L.L.C., Woodland Hills, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/603,864

(22) Filed: Jun. 26, 2000

Related U.S. Application Data

(63) Continuation of application No. 09/145,042, filed on Sep. 1, 1998, now Pat. No. 6,080,783.
(51) Int. Cl.$^7$ .............................................. A61K 31/315
(52) U.S. Cl. ........................ 514/494; 514/849; 514/944; 424/400; 424/434; 424/489
(58) Field of Search ................................ 424/400, 434, 424/489; 514/494, 849, 944

(56) References Cited

U.S. PATENT DOCUMENTS

| 4,503,070 A | 3/1985 | Eby, III |
| 4,686,528 A | 8/1987 | Godfrey |
| 4,758,439 A | 7/1988 | Godfrey |
| 4,956,385 A | 9/1990 | Eby, III |
| RE33,465 E | 11/1990 | Eby, III |
| 5,002,970 A | 3/1991 | Eby, III |
| 5,095,035 A | 3/1992 | Eby, III |
| 5,286,748 A | 2/1994 | Eby, III |
| 5,409,905 A | 4/1995 | Ebby, III |
| 5,622,724 A | 4/1997 | Bryce-Smith |

OTHER PUBLICATIONS

Gutman (1941) *Modern Drug Encyclopedia,* 1941, P. 731.

Aug. 24, 1998 Response to Office Action (Pat. No. RE 33,465).

*Primary Examiner*—S. Mark Clardy
*Assistant Examiner*—Michael A. Williamson
(74) *Attorney, Agent, or Firm*—Snell & Wilmer L.L.P.

(57) ABSTRACT

A viscous gel for delivering minor effective homeopathic amount of zinc or another metal to the nasal membrane.

14 Claims, No Drawings

METHOD AND COMPOSITION FOR DELIVERING ZINC TO THE NASAL MEMBRANE

This is a Continuation of U.S. application Ser. No. 09/145,042, filed Sep. 1, 1998 now U.S. Pat. No. 6,080,783.

This invention relates to compositions and method for delivering minor effective amounts of a metal to the blood in a body.

More particularly, the invention relates to a method and composition for delivering a minor effective amount of ionic zinc to the nasal membrane.

In a further respect, the invention relates to a composition which maintains zinc in a negative ionic state for delivery to the nasal membrane.

In another respect, the invention relates to a composition which maintains a source of a metal in direct contact with the nasal membrane for an extended period of time.

The common cold is one of the most frequently occurring human illnesses and is responsible for substantial morbidity and economic loss. Ionic zinc is a known effective anti-rhinovirus agent in vitro and in vivo.

In one in vivo study reported in 1991, a double-blind clinical trial demonstrated the effectiveness of orally administered zinc gluconate/glycerine lozenges. The lozenges used in the study contained twenty-three milligrams of zinc provided by 179 milligrams of zinc gluconate trihydrate which provided a 13.1 millimolar ionic zinc concentration in the oral cavity. During the study, lozenges administered at two hour intervals resulted in a forty-two percent reduction in mean cold duration and in a marked reduction in both the number and severity of symptoms if treatment with the lozenges was initiated within two days of the onset of cold symptoms. A second study reported in 1992 (Zarmebo J. E., Godfrey J. C., Godfrey N., *J. Pharmm Sci* 1992; 81: 128–130) confirmed the findings of the 1991 study. Soon after the results of these studies became widely known, a number of companies began marketing their own versions of the zinc lozenge cold remedy.

While zinc lozenges are usually beneficial in treating a cold, the lozenges have several drawbacks. First, the majority of zinc in a zinc gluconate lozenge is released in the oral cavity. The principal site, however, of antiviral activity is believed to be the nasal cavity (Novick S. G., Godfrey J. C., Godfrey N. J., Wilder H. R., *Medical Hypothesis* 1996; 46: 295–302). It is surmised that some ionic zinc released by a lozenge in the oral cavity makes its way to nasal passages where the zinc binds to viral ICAM-1 receptors and inhibits rhinovirus from binding to and infecting nasal mucosal cells. The difficult encountered by ionic zinc in attempting to travel from the oral cavity to the nasal cavity limits the effectiveness of zinc lozenges. Further, in a congested individual the route from the oral cavity to the nasal cavity may be completely blocked, rendering zinc lozenges ineffective.

A second disadvantage associated with zinc lozenges is production of significant side effects. In one study, twenty percent of the subjects complained of nausea and eight percent complained of bad taste reactions (Novick S. G., Godfrey J. C., Godfrey N. J., Wilder H. R., *Medical Hypothesis* 1996; 46: 295–302). With respect to the nausea, it is well established that excessive zinc in the intestinal tract interferes with copper absorption and that preventing the absorption by the body of sufficient quantities of copper can lead to a variety of undesirable pathological states. The overuse of zinc lozenges may contribute to copper depletion.

We have discovered a novel composition and method for delivering ionic (negatively charged) zinc to the nasal membrane without encountering the disadvantages normally associated with zinc lozenges. The composition maintains ionic zinc in direct contact with the nasal membrane, preferably for an extended period of time of at least one-quarter hour, and delivers rapidly zinc into the nasal membrane and into blood in the nasal membrane. The composition includes from 90% to 99.1 by weight of at least one carrier and 0.9% to 2.0% by weight (from about 20 mM to 44 mM), preferably 0.9% to 1.5% (from about 20 mM to 33 mM), zinc gluconate. Each 0.1% by weight zinc gluconate in the composition produces a concentration of approximately 0.014% by weight ionic zinc (i.e., of about 2.2 mM ionic zinc). At least a 20 mM concentration of ionic zinc is preferred in the composition to insure that a sufficiently high concentration of ionic zinc is produced by the composition at the interface between the composition and the nasal membrane.

The composition has a viscosity in the range of 5,000 to 20,000 centipoise. The viscosity of the composition is important because it facilitates maintenance of the composition in the nasal cavity in contact with the nasal membrane or with mucous on the membrane. When the viscosity is less than about 5,000 centipoise, the composition tends to be drawn by gravity out of the nasal cavity. If the viscosity is in excess of about 20,000 centipoise, the thickness of the composition interferes with the diffusion of ionic zinc through the composition to the nasal membrane. During the development of the composition of the invention, nasal sprays were considered and discarded because the low viscosity of the liquids comprising such sprays allows the liquids to flow under gravity out of the nasal cavity, preventing the sprays from contacting the nasal membrane for an extended period of time. The effectiveness of a nasal spray usually substantially dissipates in less than five minutes. Similarly, applying the composition on a swab or nose plug is not believed efficient because the swab or nose plug, which may for example be made of cotton or of a sponge material retains the composition and interferes with the delivery of an additional supply of the composition into contact with the nasal membrane following dissipation of the composition which is on the surface of the swab or plug and is in direct contact with the nasal membrane.

As noted, nasal sprays were avoided during development of the invention. By way of background with respect to zinc—bearing nasal sprays, U.S. Pat. No. 5,688,532 concerns antiallergic spray preparations and discloses and claims a method for the treatment of an allergic condition in which a spray solution is applied to the eye or respiratory tract of a mammal having the allergic condition. The spray solution includes a non-toxic, anti-allergy effective amount of ionic zinc in a concentration below that which causes irritation to mucus membranes. The majority of the ionic zinc in the spray solution is unchelated zinc and is in the form of free ionic solution, wherein the solution has a zinc ion content of between about 0.002 and about 0.12% (w/v). The allergic condition treated with the spray solution can comprise hay-fever and asthma. The spray solution can be selected from the group consisting of essentially aqueous and essentially saline solutions; can have a zinc ion content of about 0.04% (w/v); can comprise a mineral acid salt of zinc as solute; can comprise a solute selected from the group consisting of zinc sulfate and zinc chloride; can be dispensed in aliquots of about either 0.05 to 0.5 ml or 0.2 ml; and/or, can include at least one other pharmaceutically acceptable ingredient. The other pharmaceutically acceptable ingredient can be selected from the group consisting of antihistamines, scenting agents and active ingredients; or, can comprise ascorbate. U.S. Pat. No. 5,688,532 also discloses and claims an improvement in a method for treatment of an allergic condition by the administration of a zinc compound to a mammal possessed of an allergic condition. The improvement consists essentially of spraying a solution comprising a non-toxic, anti-allergy effective amount of ionic zinc to the eye or respiratory tract of a mammal possessing the allergic condition. The solution comprises a concentration of ionic zinc below that which causes irritation to mucus membranes. The majority of the ionic zinc in the spray is unchelated zinc and is in the form of free ionic solution. The solution has a zinc ion content of between about 0.002 and 0.12% (w/v). U.S. Pat. No. 5,622,724 discloses and claims a method for the treatment of the symptoms of the common cold comprising administering a spray of a solution containing a non-toxic, symptom effective treating amount of a solution of a substantially unchelated ionic zinc compound. The solution contains substantially unchelated zinc ions in a concentration of from about 0.004 to about 0.12% (w/vol), to the nostrils and respiratory tract of a patient in need thereof. The solution can be selected from the group consisting of aqueous and saline solutions; can further comprise an effective amount of a flavor and/or odor enhancing agent; can have an unchelated zinc ion content of about 0.04% (w/v); or, can consist essentially of the substantially unchelated ionic zinc compound and at least one pharmaceutically acceptable carrier. The substantially unchelated ionic zinc compound can comprise a mineral acid salt of zinc; can comprise a salt selected from the group consisting of zinc sulfate and zinc chloride; or, can comprise zinc sulfate. Utilization of zinc chloride at concentrations greater than 0.2%, especially greater than 0.4% is not preferred because, as is well known in the art, zinc chloride is caustic.

The carrier utilized in the invention can include 0.05% to 3.0% by weight glycerine. The glycerine is important and is presently preferred because it allows zinc to remain in a negative ionic state until the zinc contacts the nasal membrane and/or mucous on the nasal membrane. One problem encountered during development of the invention was identifying a carrier which maintains zinc in an ionic state.

The composition of the invention preferably permits ionic zinc to diffuse through the composition to the nasal epithelial membrane or mucous on the epithelial membrane. This facilitates the availability of a continuous supply of ionic zinc because the composition will continue via diffusion to supply zinc without requiring that the portion of the composition adjacent the nasal epithelial membrane (on mucous on the membrane) dissolve or dissipate and expose a fresh portion of the composition containing ionic zinc. As noted, composition viscosities in excess of about 20,000 centipoise are believed to interfere with the diffusion of zinc through the composition. Viscosity measurements recited herein were obtained using the Brookfield Syncho-Lectric Viscometer for the measurement of the apparent Viscosity of Newtonian and Non-Newtonian materials at low shear rates at given rotational speeds (ASTM D1824-87). Spindle 4 for a viscosity less than 8,000 centipoise; spindle 6 or a viscosity of 8,000 centipoise or greater. See also ASTM D1084-88, ASTM D2196-86 and other ASTM protocols concerning the measurement of viscosity.

We have also discovered a method of delivering minor effective amounts of a metal into the blood. The method includes the step of providing a viscous delivery composition. The delivery composition includes 90% to 99.995% by weight of at least one carrier and less than 1.5% by weight of the metal. The composition has a viscosity in the range of 5,000 to 20,000 centipoise. The method includes the additional steps of applying the delivery composition in the nasal cavity in direct contact with the nasal membrane, and maintaining the delivery composition in contact with the nasal membrane for at least one-quarter hour.

The following examples depict the presently preferred embodiments of the invention for the purposes of illustrating the practice thereof and not by way of limitation of the scope of the invention. In the examples, all proportions are by weight, unless otherwise noted.

EXAMPLE 1

One thousand ounces of a zinc gel is prepared by mixing together purified water, glycerin, carbopol, and zinc gluconate. The gel includes:

| Component | Weight Percent |
| --- | --- |
| PURIFIED WATER | 95.8 |
| GLYCERIN U.S.P | 2.0 |
| CARBOPOL 940 nf | 0.5 |
| ZINC (IONIC) | 0.21 (33.3 mM) |
| ZINC GLUCONATE (source of ionic zinc) | 1.50 (33.3 mM) |

The concentration of zinc gluconate in the gel composition of the invention is preferably in the range of 0.9% to 2.0% (20 mM to 44 mM), preferably 0.9% to 2.0%, by weight. The carrier in the gel composition can vary as desired, but presently preferably includes 90.0 to 99.0% purified water, 0.05 to 3.0% by weight glycerine (a thickener which also functions to permit zinc to maintain its ionic state), and 0.5% to 3.0% by weight of a carbohydrate or other thickener. A carbohydrate thickener is presently preferred. Other thickeners which can be utilized include: carrageenan, sugar, guar gum, and methylcellulose. The glycerine in the carrier produces a matrix which permits zinc ions to readily diffuse therethrough. The glycerine is also preferred because it has the ability to dissolve into and permeate mucous and the nasal epithelial membrane, carrying with it ionic zinc.

EXAMPLE 2

One ounce of the zinc gel of Example 1 is placed in the nasal cavity of a healthy thirty-nine year old male Caucasian. The gel remains in contact with at least a portion of the nasal epithelial membrane or the mucous layer on the membrane. After four hours the zinc gel has completely dissipated.

EXAMPLE 3

Example 2 is repeated, except the individual is a twenty-four year old African American who has been experiencing mild cold symptoms for one day. The gel remains in contact with at least a portion of the nasal epithelial membrane or the mucous layer on the membrane. After four hours the zinc gel has completely dissipated and the individual notices a marked reduction in the severity of his cold symptoms.

EXAMPLE 4

Example 3 is repeated, except that the zinc gel of the invention is not administered to the twenty-four year old African American, nor is any other medication. After four hours, he does not notice any reduction in the severity of his cold symptoms.

EXAMPLE 5

Examples 3 and 4 are repeated, except the individual treated is a fifteen year old Japanese girl who has been suffering from mild cold symptoms for a day. Similar results are obtained.

EXAMPLE 6

Examples 3 and 4 are repeated, except the individual treated is a fifty year old Caucasian man who has been suffering from cold symptoms for two days. Similar results are obtained.

EXAMPLE 7

Example 2 is repeated except that the concentration of zinc in the nasal mucosa is measure just prior to insertion of the zinc gel; and, one, two, three, and four hours after the gel is inserted in the individual's nasal cavity. The following results are obtained:

| Time of Measurement | Zinc Concentration (Wt. %) |
| --- | --- |
| Just prior to administration of zinc gel | 0.003% |
| Ten minutes after administration of zinc gel | 0.008% |
| One-half hour after administration of zinc gel | 0.01% |
| One hour after administration of zinc gel | 0.01% |
| Two hours after administration of zinc gel | 0.011% |
| Three hours after administration of zinc gel | 0.012% |
| Four hours after administration of zinc gel | 0.012% |

EXAMPLE 8

Examples 1 to 6 are repeated, except that the concentration of ionic zinc in the composition is 20 mM instead of 30.0 millimolar. Similar results are obtained.

EXAMPLE 9

Example 1 to 6 are repeated, except that the concentration of ionic zinc in the composition is 44 mM instead of 30.0 millimolar. Similar results are obtained.

EXAMPLE 10

Examples 1 to 6 are repeated, except that the concentration of ionic zinc in the composition is 33 mM instead of 15.0 millimolar. Similar results are obtained.

One of the objectives of the invention is the delivery into the blood via the nasal membrane homeopathic concentrations of metals or other chemical elements or compositions. This ordinarily requires the delivery of specific selected titrated concentrations (i.e., minor effective amounts) of a component. If a component is delivered to the blood stream in a concentration which is too high, this can have an inadverse effect in the body. The delivery of minor effective amounts of components to the blood stream via the nasal membrane in accordance with the invention is believed highly advantageous because it offers a rapid delivery into the blood stream of selected metered minor effective amounts of a metal or other chemical element(s) or composition(s). Attempting to deliver orally homeopathic titrated amounts of chemical elements or compositions is not believed practical because of the degradation of chemical elements which occurs in the oral cavity.

Zinc in the nasal cavity acts as a decongestant, enhancing the discharge of mucous and inhibiting the generation of new mucous. Menthol is also a decongestant and can be incorporated in the composition of the invention in a concentration of 0.01% to 0.10% by weight. Menthol is a bronchial dilator, functioning to open air passages in the lungs and to help discharge mucous.

When the zinc gel of the invention is applied to the nasal cavity, zinc ions diffuse from the gel matrix into the mucous or mucous membrane in the nasal cavity. It is believed that the zinc concentration in the mucous or mucous membrane creates a barrier which inhibits viral infection of the nasal epithelial membrane. As ionic zinc is absorbed from the gel into the mucous membrane and other nasal epithelial cells, the gel matrix permits new zinc to diffuse into the nasal membrane. The gel matrix has micelle cell—like properties which facilitate the diffusion of zinc through the gel matrix.

The homeopathic concentration of zinc ions in the zinc gel of the invention is 20 millimolar (mM) to 44 millimolar, preferably 20 mM to 33 mM. Concentrations of zinc in excess of 44 mM are not preferred.

As would be appreciated by those of skill in the art, various carriers can be developed to deliver any desired metal, pharmaceutical, or other chemical element or component into the blood stream via the nasal membrane, either in homeopathic or other desired concentrations.

Having described our invention in such terms as to enable those skilled in the art to understand and practice it, and having identified the presently preferred embodiments thereof.

We claim:

1. A method of delivering zinc to a nasal membrane, the method comprising the steps of:

providing a zinc composition having a viscosity between about 5,000 and about 20,000 centipoise; and applying said composition to a nasal cavity.

2. The method of claim 1, wherein said applying step includes supplying about 1 ounce of said composition to the nasal cavity.

3. The method of claim 1, wherein said applying step includes spraying said composition into a portion of a nasal cavity.

4. The method of claim 1, wherein said applying step includes supplying a zinc composition having a zinc concentration in the range of about 15 mM to about 40 mM.

5. The method of claim 1, wherein said applying step includes supplying a zinc composition having a zinc gluconate concentration in the range of about 0.9 to about 2.0 weight percent.

6. A method of reducing a duration of a common cold symptom, the method comprising the steps of:

providing a zinc gel composition including about 0.9 to about 2.0 weight percent zinc gluconate; and applying said composition to a nasal membrane.

7. The method of claim 6, wherein said applying step includes spraying said composition.

8. The method of claim 6, wherein said applying step includes providing zinc ions configured to bind to viral ICAM-1 receptors.

9. A composition for reducing a duration of a common cold comprising:
   about 90 to about 99.1 weight percent of a carrier; and
   about 0.9 to about 2.0 weight percent zinc gluconate,
   wherein said composition has a viscosity greater than about 5,000 centipoise.

10. The composition of claim 9, wherein said carrier includes glycerin.

11. The composition of claim 10, wherein said carrier includes about 0.05 to about 3.0 weight percent glycerin.

12. The composition of claim 9, further comprising a thickener.

13. The composition of claim 12, wherein said thickener is selected from the group consisting of: carbohydrate thickeners, carrageenan, sugar, guar gum, and methylcellulose.

14. The composition of claim 9, further comprising about 0.01 to about 0.10 weight percent methanol.

* * * * *